United States Patent [19]

Grasselli et al.

[11] 4,093,558

[45] June 6, 1978

[54] MOLYBDATE CATALYSTS

[75] Inventors: Robert K. Grasselli, Chagrin Falls; Dev D. Suresh, Warrensville Heights; Robert C. Miller, Northfield, all of Ohio

[73] Assignee: The Standard Oil Company, Cleveland, Ohio

[21] Appl. No.: 492,374

[22] Filed: Jul. 29, 1974

Related U.S. Application Data

[62] Continuation-in-part of Ser. No. 313,495, Dec. 8, 1972, abandoned, which is a Division of Ser. No. 67,269, Aug. 26, 1970, abandoned.

[51] Int. Cl.$^2$ ............................................. B01J 21/02
[52] U.S. Cl. ................................... 252/432; 252/435; 252/437; 252/439; 252/464; 252/469; 252/470
[58] Field of Search ............... 252/432, 435, 437, 439, 252/464, 469, 470

[56] References Cited

U.S. PATENT DOCUMENTS

| | | | |
|---|---|---|---|
| 2,360,689 | 10/1974 | Kipper | 252/470 |
| 2,625,519 | 1/1953 | Hartig | 252/435 |
| 3,358,020 | 12/1967 | Hendrickx | 252/461 |
| 3,446,840 | 5/1969 | Kato et al. | 252/432 X |
| 3,542,843 | 11/1970 | Yoshino et al. | 252/432 X |
| 3,668,147 | 6/1972 | Yoshino et al. | 252/439 |
| 3,716,496 | 2/1973 | Yoshino et al. | 252/439 |
| 3,746,650 | 7/1973 | Shiraishi et al. | 252/437 |
| 3,904,653 | 9/1975 | Milberger et al. | 252/470 |

FOREIGN PATENT DOCUMENTS

| | | |
|---|---|---|
| 1,157,117 | 7/1969 | United Kingdom. |
| 903,034 | 8/1962 | United Kingdom. |

OTHER PUBLICATIONS

Chemical Abstracts, vol. 71, (1969), 114953j, Abstract of Romanian Pat. 51,772, Jul. 26, 1969.

*Primary Examiner*—Patrick P. Garvin
*Assistant Examiner*—John P. Sheehan
*Attorney, Agent, or Firm*—David J. Untener; Herbert D. Knudsen; Larry W. Evans

[57] ABSTRACT

The present invention is molybdate catalysts composed of the combined oxides of the elements antimony, molybdenum and at least one member selected from the group consisting of iron and vanadium and optionally one or more oxides of aluminum, boron, tellurium, chromium, cobalt, nickel, copper, bismuth, phosphorus and tungsten.

11 Claims, No Drawings

MOLYBDATE CATALYSTS

This is a continuation-in-part of Ser. No. 313,495, filed Dec. 8, 1972, which is a division of Ser. No. 67,269, filed Aug. 26, 1970, both now abandoned.

SUMMARY OF THE INVENTION

This invention relates to molybdate catalysts comprising antimony, molybdenum, and at least one member selected from the group consisting of iron and vanadium. These catalysts were especially useful for preparing maleic anhydride from hydrocarbons.

The catalyst employed in the process of this invention can be used alone or supported on or impregnated in a carrier material such as silica, alumina, zirconia, calcium-stabilized zirconia, thoria, boron phosphate, silicon carbide, pumice, clay, diatomaceous earth or titania. In general, this support may be employed in amounts less than 95 percent by weight of the final catalyst composition.

The catalysts embodied herein may be calcined to produce desirable physical properties such as attrition resistance, optimum surface area and particle size. It is generally preferred that the calcined catalyst be further heat-treated in the presence of oxygen and at a temperature of about 500° F. but below a temperature deleterious to the catalyst.

The catalysts most useful in this invention are those having the formula $$A_a X_b Sb_c Mo_d O_e$$

wherein

A is at least one member selected from the group consisting of iron and vanadium;

X is at least one member selected from the group consisting of aluminum, chromium, cobalt, nickel, copper, bismuth, tellurium, boron, phosphorus and tungsten;

and wherein $a$ is a number from 0.1 to 6;
$b$ is a number from 0 to 3;
$c$ is a number from 0.1 to 12;
$d$ is 12; and
$e$ is a number determined by the valence requirements of the combined valences of the elements other than oxygen present in the catalyst.

The catalysts of this invention can be prepared by dissolving or slurrying salts of their respective metals in water or acid and heating the mixture with an aqueous silica dispersion until a gel forms. After gelation, the resulting mixture is heated at 130° C. until dry. The catalyst is then heated at about 300° C. for four hours and calcined at 800° F. in air for an additional twenty-four hours. In some instances, the catalysts were also further treated in air for three hours at 1200° F.

The catalysts preferably are heat-treated in the presence of molecular oxygen in the range of about 800° F. to 1600° F. before they are employed in the present process.

SPECIFIC EMBODIMENTS

EXAMPLE 1

A catalyst composed of 80 percent by weight of $VFeSb_3Mo_{12}O_{48}$ and 20 percent by weight of $SiO_2$ was prepared from a mixture of:

| | |
|---|---|
| 3.9 g. $NH_4VO_3$ | (0.033 mole V) |
| 13.5 g. $Fe(NO_3)_3 \cdot 9H_2O$ | (0.033 mole Fe) |
| 14.5 g. $Sb_2O_3$ | (0.100 mole Sb) |
| 60 cc. $HNO_3$ | (70 percent by Weight aqueous solution) |
| 70.6 g. $(NH_4)_6Mo_7O_{24} \cdot 4H_2O$ | (0.400 mole Mo) |
| 66.4 g. Ludox AS (DuPont) | (30 percent aqueous solution of $SiO_2$) |

The antimony oxide was oxidized with the nitric acid on a hotplate with constant stirring for about 30 minutes. Water slurries or solutions of the other compounds listed above were then added with heating and stirring was continued until the mixture started to gel. The product was dried in an oven (270° F.) overnight. The catalyst was then heat-treated in air at 800° F. for 16 hours and then at 1200° F. in air for three hours. The final catalyst was found to have a surface area of 17 square meters per gram.

In general, the single pass conversion of n-butane to maleic anhydride increases with on-stream time until an optimum which can be sustained is reached.

Maleic anhydride was produced from n-butane in a vapor phase reactor over a fixed bed of the catalyst described above. In this reaction a standard fixed bed 5 cc. upflow reactor was used and a temperature of 450° C. was employed. The molar ratio of n-butane-to-air in the feed was 1:25 and an apparent contact time of one second was used with the following results:

| On-Stream Time (Hrs.) | Single Pass Mole % Conversion of N-Butane to Maleic Anhydride | Single Pass Weight % Conversion of N-Butane to Maleic Anhydride |
|---|---|---|
| 0.5 | 9.8 | 16.6 |
| 1 | 12.1 | 20.5 |
| 20 | 16.2 | 27.4 |
| 70 | 20.1 | 34.0 |

EXAMPLE 2

A catalyst having a composition of 80 percent by weight of $BFeVSb_3Mo_{12}O_{45}$ and 20 percent by weight of $SiO_2$ was prepared by the procedure of Example 1 from the following ingredients:

| | |
|---|---|
| 3.9 g. $NH_4VO_3$ | (0.033 mole V) |
| 2.1 g. $H_3BO_3$ | (0.033 mole B) |
| 13.5 g. $Fe(NO_3)_3 \cdot 9H_2O$ | (0.033 mole Fe) |
| 14.5 g. $Sb_2O_3$ | (0.1 mole Sb) |
| 58 cc. $HNO_3$ | (70 percent by weight aqueous solution) |
| 70.6 g. $(NH_4)_6Mo_7O_{24} \cdot 4H_2O$ | (0.4 mole Mo) |
| 67.2 g. Ludox AS | (30 percent aqueous solution of $SiO_2$) |

The final catalyst was dried and heat-treated at 800° F. for 16 hours and at 1200° F. for 19 hours. The surface area of the catalyst was 24 square meters per gram.

N-butane was converted to maleic anhydride according to the procedure described in Example 1 using this catalyst. A single pass conversion of 18.1 mole percent (30.6 percent by weight) of maleic anhydride was achieved after 5.0 hours on stream.

EXAMPLE 3

A catalyst composed of 80 percent by weight of $PFeVSb_3Mo_{12}O_{50}$ and 20 percent by weight of $SiO_2$ was prepared by the procedure of Example 1 except that $NH_4VO_3$ was included in the proper preparation.

N-butane was converted to maleic anhydride according to the procedure of Example 1 using the foregoing catalyst. A single pass conversion of 10.9 mole percent (18.4 percent by weight) of maleic anhydride was achieved.

EXAMPLE 4

A catalyst composed of 80 percent by weight of TeFeVSb$_3$Mo$_{12}$O$_{51}$ and 20 percent by weight of SiO$_2$ was prepared by a procedure similar to that described in Example 1.

N-butane was converted to maleic anhydride with the foregoing catalyst according to the procedure described in Example 1. A single pass conversion of 17.1 mole percent (28.9 percent by weight) of maleic anhydride was achieved

EXAMPLE 5

A catalyst composed of 80 percent by weight of Bi$_{0.5}$FeVSb$_3$Mo$_{12}$O$_{49}$ and 20 percent by weight of SiO$_2$ was prepared by a procedure similar to that described in Example 1.

N-butane was converted to maleic anhydride with the foregoing catalyst according to the procedure described in Example 1. A single pass conversion of 14.7 mole percent (24.8 percent by weight conversion) of n-butane to maleic anhydride was achieved.

EXAMPLE 6

A catalyst which was free of any carrier and had the composition of 100 percent by weight of FeVSb$_3$Mo$_{12}$O$_{48}$ was prepared by the procedure of Example 1 except that the use of SiO$_2$ sol was eliminated.

N-butane was converted to maleic anhydride with the foregoing catalyst according to the procedure of Example 1. A single pass conversion of n-butane to maleic anhydride of 13.9 mole percent (23.6 percent by weight) was achieved.

We claim:

1. A molybdate catalyst of the formula $$A_a X_b Sb_c Mo_d O_e$$

wherein
  A is selected from the group consisting of iron or iron and vanadium;
  X is at least one element selected from the group consisting of aluminum, chromium, cobalt, nickel, copper, bismuth, tellurium, boron, phosphorus, titanium and tungsten;
and wherein
  $a$ is a number from 0.01 to 2;
  $b$ is a number from 0 to 3;
  $c$ is a number from 0.1 to 12;
  $d$ is 12; and
  $e$ is a number as determined by the combined valence requirement of the elements other than oxygen present in the catalyst.

2. The catalyst of claim 1 which is VFeSb$_3$Mo$_{12}$O$_{48}$.
3. The catalyst of claim 1 which is Fe$_2$Sb$_3$Mo$_{12}$O$_{47}$.
4. The catalyst of claim 1 wherein the catalyst is BFeVSb$_3$Mo$_{12}$O$_{49}$.
5. The catalyst of claim 1 wherein A is iron.
6. The catalyst of claim 1 wherein A is iron and vanadium.
7. The catalyst of claim 1 wherein X is boron.
8. The catalyst of claim 1 wherein X is chromium.
9. The catalyst of claim 1 wherein X is phosphorus.
10. The catalyst of claim 1 wherein X is titanium.
11. The catalyst of claim 1 wherein X is copper.

* * * * *